US007011968B1

(12) United States Patent
Walter et al.

(10) Patent No.: US 7,011,968 B1
(45) Date of Patent: Mar. 14, 2006

(54) FRAGMENTS OF VIRUS PROTEIN 2 OR 3 OF THE POLYOMA VIRUS, USED FOR TRANSPORTING ACTIVE INGREDIENTS

(75) Inventors: Jurgen Walter, Erlangen (DE); Christian Reiser, Bamberg (DE); Wolf Bertling, Erlangen (DE)

(73) Assignee: november Aktiengesellschaft Gesellschaft fur Molekulare Medizin, Erlangen (DE)

( * ) Notice: Subject to any disclaimer, the term of this patent is extended or adjusted under 35 U.S.C. 154(b) by 0 days.

(21) Appl. No.: 09/958,451

(22) PCT Filed: Apr. 3, 2000

(86) PCT No.: PCT/DE00/00976

§ 371 (c)(1),
(2), (4) Date: May 28, 2002

(87) PCT Pub. No.: WO00/61616

PCT Pub. Date: Oct. 19, 2000

(30) Foreign Application Priority Data

Apr. 10, 1999 (DE) ................................ 199 16 224

(51) Int. Cl.
*C12N 7/00* (2006.01)
*A61K 9/00* (2006.01)
*A61K 9/14* (2006.01)

(52) U.S. Cl. ................... 435/235.1; 530/350; 530/402; 530/403; 530/404; 530/405; 530/406; 424/192.1; 424/193.1; 424/400; 424/489; 424/456; 424/499; 424/780

(58) Field of Classification Search ............. 435/235.1; 424/456, 193.1, 192.1, 204.1, 400, 780, 489, 424/499; 530/350, 402, 403, 404, 405, 406
See application file for complete search history.

(56) References Cited

U.S. PATENT DOCUMENTS

| | | | | |
|---|---|---|---|---|
| 4,950,599 A | | 8/1990 | Bertling | |
| 5,618,536 A | * | 4/1997 | Lowy et al. ............. | 424/192.1 |
| 6,165,772 A | * | 12/2000 | Bertling ................... | 435/235.1 |

FOREIGN PATENT DOCUMENTS

| | | |
|---|---|---|
| DE | 43 35 025 | 4/1995 |
| DE | 195 43 553 A1 | 5/1997 |
| EP | 0 259 149 A2 | 3/1988 |
| GB | 2 257 431 | 1/1993 |
| WO | WO 94/04686 | 3/1994 |
| WO | WO 96/11274 | 4/1996 |
| WO | WO9743431 | * 11/1997 |

OTHER PUBLICATIONS

Chang et al (Transactions of the Kansas Academy of Science 96:35-39, 1993).*

Jans et al (Medicinal Research Reviews 18(4):189-223, 1998).*

Shah. Fields Virology, Third edition, ed. Fields et al, Lippincott-Raven Oublishers, Philadelphia, 2996, pp. 2027-2043.*

Cole. Fields Virology, Third edition, ed. Fields et al, Lippincott-Raven Oublishers, Philadelphia, 2996, pp. 1997-2025.*

Chen et al (EMBO Journal 17:3233-3240, 1998).*

Barouch et al (Journal of Virology 68:3982-3989, 1994).*

Albericio et al., “Use of the Npys thiol protection in solid phase peptide synthesis,” *Int. J. Peptide Protein Res.,* 1989, 34:124-128.

Atherton and Sheppard, *Solid Phase Peptide Synthesis—A Practical Approach,* 1989, IRL Press at Oxford University Press, Oxford (Table of Contents only).

Chen et al., “Interaction of polyomavirus internal protein VP2 with the major capsid protein VP1 and implications for participation of VP2 in viral entry,” *EMBO J.,* 1998, 17(12): 3233-3240.

DeFoort et al., “A rational design of synthetic peptide vaccine with a built-in adjuvant,” *Int. J. Peptide Protein Res.,* 1992, 40:214-221.

Lindner and Robey, “Automated synthesis and use of N-chloroacetyl-modified peptides for the preparation of synthetic peptide polymers and peptide-protein immunogens,” *Int. J. Peptide Protein Res.,* 1987, 30:794-800.

Redmond et al., “Rotavirus Particles Function as Immunological Carriers for the Delivery of Peptides from Infectious Agents and Endogenous Proteins,” *Mol. Immunol.,* 1991, 28(3):269-278.

Schnorrenberg and Gerhardt, “Fully Automatic Simultaneous Multiple Peptide Synthesis in Micromolar Scale—Rapid Synthesis of Series of Peptides for Screening in Biological Assays,” *Tetrahedron,* 1989, 45(24):7759-7764.

Zhang and Tam, “Synthesis and Application of Unprotected Cyclic Peptides as Building Blocks for Peptide Dendrimers,” *J. Am. Chem. Soc.,* 1997, 119:2363-2370.

Abbing et al., “Efficient Intracellular Delivery of a Protein and a Low Molecular Weight Substance via Recombinant Polyomavirus-like Particles,” *J. Biol. Chem.,* 2004, 279(26): 27410-21.

* cited by examiner

*Primary Examiner*—Mary E. Mosher
(74) *Attorney, Agent, or Firm*—Fish & Richardson P.C., P.A.

(57) ABSTRACT

The invention relates to a synthetic, biologically active molecule for fixing an active ingredient to the virus protein 1 (VP1) of the polyoma virus. According to the invention, an amino acid sequence A1 which is derived from the C-terminal end of virus protein 2 (VP2) or 3 (VP3) of the polyoma virus is bonded to an active ingredient at one of its ends.

38 Claims, No Drawings

SEQUENCE LISTING

<160> NUMBER OF SEQ ID NOS: 6

<210> SEQ ID NO 1
<211> LENGTH: 11

-continued

```
<212> TYPE: PRT
<213> ORGANISM: Polyoma virus sp.
<300> PUBLICATION INFORMATION:
<301> AUTHORS: Chen, Xiaojiang S.
      Stehle, Thilo
      Harrison, Stephen C.
<302> TITLE: Interaction of polyomavirus internal protein VP2
<303> JOURNAL: The EMBO Journal
<304> VOLUME: 17
<305> ISSUE: 12
<306> PAGES: 3233-3240
<307> DATE: Jun-1998

<400> SEQUENCE: 1

Trp Met Leu Pro Leu Ile Leu Gly Leu Tyr Gly
 1               5                  10


<210> SEQ ID NO 2
<211> LENGTH: 33
<212> TYPE: PRT
<213> ORGANISM: Artificial Sequence
<220> FEATURE:
<223> OTHER INFORMATION: Residues 1-21 of Reverse Transcriptase from
      HIV-1; Residues 22-33 of polyoma VP2

<400> SEQUENCE: 2

Leu Ala Glu Asn Arg Glu Ile Leu Lys Glu Pro Val His Gly Val Tyr
 1               5                  10                  15

Tyr Asp Pro Ser Lys Pro Asp Trp Met Leu Pro Leu Ile Leu Gly Leu
            20                  25                  30

Tyr


<210> SEQ ID NO 3
<211> LENGTH: 34
<212> TYPE: PRT
<213> ORGANISM: Polyoma virus sp.
<300> PUBLICATION INFORMATION:
<301> AUTHORS: Chen, Xiaojiang S.
      Stehle, Thilo
      Harrison, Stephen C.
<302> TITLE: Interaction of polyomavirus internal protein VP2
<303> JOURNAL: The EMBO Journal
<304> VOLUME: 17
<305> ISSUE: 12
<306> PAGES: 3233-3240
<307> DATE: Jun-1998

<400> SEQUENCE: 3

Gln Asp Glu Ser Gly Glu Val Ile Lys Phe Tyr Gln Ala Gln Val Val
 1               5                  10                  15

Ser His Gln Arg Val Thr Pro Asp Trp Met Leu Pro Leu Ile Leu Gly
            20                  25                  30

Leu Tyr


<210> SEQ ID NO 4
<211> LENGTH: 318
<212> TYPE: PRT
<213> ORGANISM: Polyoma virus sp.
<300> PUBLICATION INFORMATION:
<301> AUTHORS: Chen, Xiaojiang S.
      Stehle, Thilo
      Harrison, Stephen C.
<302> TITLE: Interaction of polyomavirus internal protein VP2
<303> JOURNAL: The EMBO Journal
<304> VOLUME: 17
<305> ISSUE: 12
<306> PAGES: 3233-3240
<307> DATE: Jun-1998
```

-continued

<400> SEQUENCE: 4

```
Met Gly Ala Ala Leu Thr Ile Leu Val Asp Leu Ile Glu Gly Leu Ala
 1               5                  10                  15

Glu Val Ser Thr Leu Thr Gly Leu Ser Ala Glu Ala Ile Leu Ser Gly
            20                  25                  30

Glu Ala Leu Ala Ala Leu Asp Gly Glu Ile Thr Ala Leu Thr Leu Glu
        35                  40                  45

Gly Val Met Ser Ser Glu Thr Ala Leu Ala Thr Met Gly Ile Ser Glu
    50                  55                  60

Glu Val Tyr Gly Phe Val Ser Thr Val Pro Val Phe Val Ser Arg Thr
65                  70                  75                  80

Ala Gly Ala Ile Trp Leu Met Gln Thr Val Gln Gly Ala Ser Thr Ile
                85                  90                  95

Ser Leu Gly Ile Gln Arg Tyr Leu His Asn Glu Glu Val Pro Thr Val
            100                 105                 110

Asn Arg Asn Met Ala Leu Ile Pro Trp Arg Asp Pro Ala Leu Leu Asp
        115                 120                 125

Ile Tyr Phe Pro Gly Val Asn Gln Phe Ala His Ala Leu Asn Val Val
    130                 135                 140

His Asp Trp Gly His Gly Leu Leu His Ser Val Gly Arg Tyr Val Trp
145                 150                 155                 160

Gln Met Val Val Gln Glu Thr Gln His Arg Leu Glu Gly Ala Val Arg
                165                 170                 175

Glu Leu Thr Val Arg Gln Thr His Thr Phe Leu Asp Gly Leu Ala Arg
            180                 185                 190

Leu Leu Glu Asn Thr Arg Trp Val Val Ser Asn Ala Pro Gln Ser Ala
        195                 200                 205

Ile Asp Ala Ile Asn Arg Gly Ala Ser Ser Ala Ser Ser Gly Tyr Ser
    210                 215                 220

Ser Leu Ser Asp Tyr Tyr Arg Gln Leu Gly Leu Asn Pro Pro Gln Arg
225                 230                 235                 240

Arg Ala Leu Phe Asn Arg Ile Glu Gly Ser Met Gly Asn Gly Gly Pro
                245                 250                 255

Thr Pro Ala Ala His Ile Gln Asp Glu Ser Gly Glu Val Ile Lys Phe
            260                 265                 270

Tyr Gln Ala Gln Val Val Ser His Gln Arg Val Thr Pro Asp Trp Met
        275                 280                 285

Leu Pro Leu Ile Leu Gly Leu Tyr Gly Asp Ile Thr Pro Thr Trp Ala
    290                 295                 300

Thr Val Ile Glu Glu Asp Gly Pro Gln Lys Lys Arg Arg Leu
305                 310                 315
```

<210> SEQ ID NO 5
<211> LENGTH: 21
<212> TYPE: PRT
<213> ORGANISM: Artificial Sequence
<220> FEATURE:
<223> OTHER INFORMATION: Residues 1-20 of Reverse Transcriptase from HIV-1 and an additional C-terminal Cys

<400> SEQUENCE: 5

```
Leu Ala Glu Asn Arg Glu Ile Leu Lys Glu Pro Val His Gly Val Tyr
 1               5                  10                  15

Tyr Asp Pro Ser Cys
            20
```

-continued

```
<210> SEQ ID NO 6
<211> LENGTH: 17
<212> TYPE: PRT
<213> ORGANISM: Artificial Sequence
<220> FEATURE:
<223> OTHER INFORMATION: Partial sequence of the GAG protein from HIV-1

<400> SEQUENCE: 6

Gly Ser Glu Glu Leu Arg Ser Leu Tyr Asn Thr Val Ala Thr Leu Tyr
 1              5                   10                  15

Cys
```

FRAGMENTS OF VIRUS PROTEIN 2 OR 3 OF THE POLYOMA VIRUS, USED FOR TRANSPORTING ACTIVE INGREDIENTS

The invention relates to a synthetic biologically active molecule and to a method for the preparation thereof.

Chen, X. S., Stehle, T. and Harrison, S. C. (1998): Interaction of polyomavirus internal protein VP2 with the major capsid protein VP1 and implications for participation of VP2 in viral entry, The EMBO Journal, Vol. 17, No. 12, pp. 3233–3240 describe the interactions responsible for anchoring virus proteins VP2 and VP3 of polyoma virus to virus protein 1. According to said publication, the anchoring takes place in the region of the C-terminal end of VP2 or VP3.

U.S. Pat. No. 4,950,599 discloses that the polyoma virus is suitable for transporting active substances into cells. Furthermore, DE 196 18 797 A1 discloses that a capsomer derived from polyoma virus is suited to transporting molecular material into cells.

EP 0 259 149 A2 discloses using the rotavirus internal capsid protein VP6 as immunological carrier molecule and as a vaccine for stimulating the immune response to rotavirus infections. In this connection, immunogenic peptides are bound to VP6 via peptide—peptide interactions which are not defined in any detail. VP6 here does not form a structural capsomer but on the contrary displays a distinctive structural polymorphism. VP6 is present as a monomer or in oligomeric form. Although oligomeric VP6 can form particles, these particles are not capsids or capsomers but unstructured carrier proteins.

Redmond, M. J. et al. (1991): Rotavirus particles function as immunological carriers for the delivery of peptides from infectious agents and endogenous proteins, Mol. Immunol. 28, 269–278 describe the use of rotavirus internal capsid protein VP6 as transport particle. In this connection, VP6 is bound to immunogenic peptides or proteins via a binding protein derived from the peptide sequence of the rotaviral protein VP4. An antigen coupled to the peptide sequence derived from VP4 is located on the outside of the transport particle and therefore is not protected from degradation.

GB 22 57 431 A describes the use of a chimeric protein which is derived from the envelope protein of phage MS-2. This protein can form capsids. Antigenic peptides or the like coupled thereto are bound to the outside of the capsid. Spontaneous assembling of the chimeric protein during expression in *E. coli* carries a high risk of contamination by bacterial DNA or proteins.

DE 43 35 025 A1 discloses an endosomolytically active virus-like particle which has been modified with membrane-active peptides on its outer surface. The preparation of said particle is complicated.

It is the object of the invention to remove the disadvantages according to the prior art. In particular it is intended to provide a simple possibility of specifically associating active substances with polyoma virus VP1.

The description makes use of the following definitions:

Derived amino acid sequence: amino acid sequence which is unchanged compared with the amino acid sequence from which it is derived, or which differs therefrom by amino acid exchanges, insertions or deletions.

C-terminal end: region or area at the C terminals.

Synthetic molecule: artificially prepared molecule.

Coupling or attaching: covalent or noncovalent binding. Noncovalent binding may be carried out, for example, via a chelate bond.

Genetic engineering: technique which includes methods for introducing defined nucleic acids into cells.

In accordance with the invention, a synthetic biologically active molecule is provided for, wherein an amino acid sequence (A1) derived from the C-terminal end of virus protein 2 (VP2) or 3 (VP3) of polyoma virus is linked to an active substance.

The proposed synthetic biologically active molecule makes it possible in a simple manner to specifically associate active substances with polyoma virus VP1. This leads to the formation of a structured capsomer. By using said capsomer it is possible to prepare in a simple manner capsids as universal carriers for active substances.

Advantageously, the amino acid sequence (A1) comprises from 10 to 55, preferably from 28 to 38, amino acids. Limitation to a relatively short amino acid sequence reduces the cost of and simplifies the preparation of the synthetic biologically active molecule.

Expediently, the amino acid sequence at least in some sections corresponds to the VP2 sequence from amino acid position 250 to 319, preferably from amino acid position 260 to 300 and particularly preferably from amino acid position 287 to 297. Said amino acid sequence ensures secure anchoring to VP1.

In the synthetic biological the amino acid sequence (A1) preferably has amino acids in the sequence below:

```
Trp Met Leu Pro Leu Ile Leu Gly Leu Tyr Gly (SEQ ID NO:1)
 1              5                  10
```

The active substance is preferably bound to the amino acid sequence (A1) via a linker. This linker may be composed of at least one amino acid, a peptide, protein, lipid or the like. The active substance may be selected from the following group: nucleic acid, oligonucleotide, protein, peptide, peptidic substance, PNA, modifications of said substances and low-molecular weight pharmaceutically active substances. Particularly suitable are those active substances which couple to the amino acid sequence via one of the reactive groups mentioned below.

The synthetic biologically active molecule may be present coupled to an amino acid sequence derived from polyoma virus VP1 and/or may be an ingredient of a medicament.

In further accordance with the invention, a method for preparing the synthetic biologically active molecule of the invention is provided for, which method has the following steps:

a) providing an amino acid sequence (A1) derived from the C-terminal end of virus protein 2 (VP2) or 3 (VP3) of polyoma virus, with the amino acid sequence (A1) having a coupling agent and b) binding the active substance to the amino acid sequence (A1) via the coupling agent.

The coupling agent may have as amino acid glycine, cysteine or glycine bound via lysine. The coupling agent is advantageously a further, preferably synthetically prepared amino acid sequence (A2) bound to the N- or C-terminal end of amino acid sequence (A1).

The synthetic biologically active molecule may be prepared, at least partly, by genetic engineering. In this connection, the amino acid sequence (A1), the further amino acid sequence (A2) and the active substance may be prepared completely or partially by genetic engineering. The further amino acid sequence (A2) expediently has glycines and/or amino acids with functional side groups, it being possible for the functional side groups to be selected from the following group: amino, sulfhydryl, carboxyl, hydroxyl, guanidinium, phenyl, indole and imidazole radical.

The coupling agent may be a reactive group bound to the C- or N-terminal end of amino acid sequence (A1) via an amino acid, preferably glycine, cysteine, or glycine bound via lysine. This may have one of the following components: amino acid with monobromoacetyl radical, amino acid with monochloroacetyl radical, amino acid with 3-nitro-2-pyridinesulfenyl radical (Npys). The proposed reactive groups can be used universally. They are suitable for coupling to a multiplicity of active substances.

It has proved particularly advantageous to bind the active substance to amino acid sequence (A1) or to the further amino acid sequence (A2) via a thioether or disulfide bridge. In practice, this kind of bond can readily be prepared. Of course, the use of other reactive groups is also conceivable. Suitable groups are, for example, N-succinimidyl bromoacetate or N-succinimidyl 3-(2-pyridylthio)propionate (SPDP).

The active substance may be bound to amino acid sequence (A1) or the further amino acid sequence (A2) via a linker. The linker may be composed of at least one amino acid, a peptide, protein, lipid, or the like.

Press, Oxford). The coupling reactions are carried out with in each case 6 equivalents of Fmoc-protected amino acid/1-hydroxybenzotriazole (HOBt)/12 equivalents of n-methylmorpholine using 2-(1H-benzotriazol-1-yl)-1,1,3,3-tetramethyluronium tetrafluoroborate (TBTU) on a polymeric carrier resin (type: Tentagel S Trityl resin, RAPP Polymere, Tubingen, Germany) with a load of 2 mmol/g of resin. The peptides contain a C-terminal COOH group.

The following protective groups are used in the synthesis: Cys (Trt), Arg (Pbf), Ser (But), Thr (But), Asp (OBut), Glu, (OBut), Asn (Trt), Gln (Trt), Lys (Boc), His (Trt), Trp (Boc), where Trt: trityl, But: t-butyl, OBut: t-butyl ester, Boc: t-butyloxycarbonyl and Pbf: 2,2,4,6,7-pentamethyldihydrobenzofuran-5-sulfonyl.

All protective groups are removed using trifluoroacetic acid (TFA)/thioanisole/thiocresol (95:2.5:2.5) at room temperature over 3 h with the addition of 3% triisopropylsilane and subsequent addition of 10% trimethylchlorosilane for 1 h. After lyophilization, the peptides are present in the form of their trifluoroacetic acid salts.

The peptides are purified by means of preparative HPLC on a Bischoff Polyencap 300 separating column, 10 μm, 250×16 mm, using a gradient of from 0.05% trifluoroacetic acid in water (eluent A) to 0.05% trifluoroacetic acid in 80% acetonitrile/water (eluent B).

Alternatively, a Vydac separating column of type 218 TP 101522 (10–15 μm, 250×22 mm) with a gradient of 43–73% eluent B in 30 min at a flow rate of 15 ml/min was used.

By means of peptide synthesis, the following amino acid sequence is synthesized, for example:

```
Trp Met Leu Pro Leu Ile Leu Gly Leu Tyr Gly (SEQ ID NO:1)
 1               5                   10
```

In further accordance with the invention, a method for preparing the synthetic biologically active molecule of the invention is provided for, which method has the following steps:

aa) synthesizing an amino acid sequence (A1) derived from the C-terminal end of virus protein 2 (VP2) or 3 (VP3) of polyoma virus and bb) coupling and synthesizing an active substance, namely a peptide, to the amino acid sequence (A1), wherein the steps under aa and under bb are carried out by means of peptide synthesis or by means of genetic engineering methods.

In step bb) the amino acid sequence (A1) is extended by the active substance. The elongation and the attaching of the active substance are carried out by repeatedly attaching amino acid residues. This method can be carried out particularly easily.

Further advantageous embodiments relating to both aforementioned methods can be found in the subclaims.

EXAMPLES

A. Synthesis and Purification of the Peptides:

Peptides are synthesized by simultaneous multiple peptides synthesis (Schnorrenberg, G. and Gerhardt, H. (1989) Tetrahedron 45, 7759) in a peptide synthesizer (type: PSSM-8 from SHIMADZU, Japan) using the 9-fluorenylmethoxycarbonyl (Fmoc)/tert. butyl (But) strategy according to Sheppard (Atherton, E. and Sheppard, R. C. (1989) "Solid phase peptide synthesis-a practical approach" IRL In this sequence, the reactive group is bound to the N-terminal end of the amino acid sequence via an amino acid, preferably via glycine. The reactive group may be composed of monochloroacetylglycine. Alternatively, it is also possible to attach a monobromoacetyl radical.

Coupling of Monochloroacetylglycine in Solid Phase Synthesis:

Equal equivalents of monochloroacetylglycine and 1-hydroxybenzotriazole (HOBt) are dissolved in dimethylformamide (DMF), mixed with an equal equivalent of N,N'-diisopropylcarbodiimide (DIC) and added to the peptide resin. Compared with the loaded peptide resin, monochloroacetylglycine is present in excess. The reaction is carried out with occasional stirring and should last for at least 1 h.

The reactive group facilitates covalent binding of the biologically active molecule prepared in this way to an active substance, for example a peptide, which has a free SH group. The reaction of the SH group with the chlorine atom of the monochloroacetyl group results in the formation of a stable thioether compound according to the following equation:

$$\text{protein-SH} + \text{Cl}-CH_2-\text{CO}-\text{Gly peptide} \xrightarrow{\text{-HCL}} \text{protein-S}-CH_2-\text{CO}-\text{Gly peptide}$$

Conjugate Formation Between a Monochloroacetyl-Modified Anchor Peptide and a Peptide having a Terminal Cysteine:

A monochloroacetyl-modified anchor peptide is used in excess of the peptide to be conjugated. The reaction is carried out in 0.1 M $NaHCO_3$ between [sic] pH 7–8 at room temperature. In the case of poor solubility of the peptide or the anchor in aqueous solution, the conjugate formation is carried out in 4 M guanidine hydrochloride, pH 8.0 (Lindner, W. and Robey, F. A. (1987) Int. J. Pept. Protein Res. 30, 794–800). Alternatively, the proportion of organic solvent, for example DMSO, in the reaction mixture can be increased. In order to avoid unwanted by-products, water-soluble phosphines may be added as reducing agent.

Optionally it is also possible to carry out the conjugation reaction under the following conditions. The monochloroacetylated anchor peptide and a peptide having a terminal SH group are incubated at room temperature in 1-methyl-2-pyrrolidone in the presence of about 10-fold excess of diisopropylethylamine and an approx. 5-fold excess of tributylphosphine. After the reaction, $H_2O$ is subsequently added and the product is precipitated by the addition of ether and purified by gel filtration (Defoort, J. P., Nardelli, B., Huang, W. and Tam, J. P. (1992) Int. J. Protein Res. 40, 214–221).

Optionally the conjugation reaction may also be carried out as follows. The peptide containing the SH group is dissolved in 0.2 M phosphate buffer, 10 mM EDTA, pH 7.4. To this mixture, the monochloroacetyl-modified anchor peptide dissolved in dimethylformamide is added. After the reaction, purification is carried out by gel filtration or RP-HPLC (Zhang, L. and Tam, J. P. (1997) J. Am. Chem. Soc. 119, 2363–2370).

Isolated VP1 pentamers are prepared by expressing VP1 as a recombinant protein with an N-terminal 6× histidine affinity tag (=His tag) in *E. coli*. The protein is purified via Ni-NTA affinity chromatography. The His tag is removed by treatment with a factor Xa. The protein is analyzed in an SDS-PAGE gel with subsequent Coomassie staining.

This starting material (VP1 protein in 20 mM Hepes, pH 7.3, 1 mM EDTA, 200 mN NaCl, 5% glycerol) is concentrated in a centricon 100 (Amincon [sic]) and separated via FPLC gel filtration (Superdex 200) with an elution buffer (50 mM Tris, 0.15 M NaCl, 5 mM EDTA, pH 8.5) into the high-molecular weight capsid fraction and the pentamer subunits (molecular weight: about 225 kD). Both fractions are concentrated in centricon 100. Iodoacetamide (SIGMA) is added to the pentamer-containing solution in a 10-fold molar excess, in order to block potentially reactive SH groups. The reaction is carried out at room temperature for 2 hours. The modified pentamer fraction is separated from excess iodoacetamide via gel filtration. VP1-specific monoclonal antibodies are adsorbed with the aid of VP1-specific antibodies and an affinity matrix (protein A support from BIO-RAD). The antibody-coated matrix is used to precipitate the purified pentamer fraction. In a further incubation step, the anchor sequence is added to the pentamer matrix. The samples are analyzed in an SDS polyacrylamide gel (12.5%).

Conjugate Formation Between an Npys-Modified Anchor Peptide and a Peptide having a Terminal Cysteine:

In addition to the reaction between a monochloro- or monobromoacetylated anchor peptide and a peptide having a terminal cysteine with formation of a thioether, the conjugate between anchor peptide and peptide sequence may optionally also be formed via the 3-nitro-2-pyridinesulfenyl (=Npys) group on a terminal cysteine of the anchor and an SH group of the peptide to be coupled. To this end, an Npys-modified cysteine instead of a monochloroacetylated glycine is coupled N- terminally to the anchor sequence. Said Npys-modified cysteine is an "activated disulfide" which is capable of reacting with thiols such as, for example, cysteines, to form an unsymmetric disulfide. This results in the removal of 3-nitro-2-thiopyridone whose UV maximum at 329 nm permits studying the kinetics of the reaction between the two compounds by spectrometry.

The following conditions are chosen for the reaction (Albericio, F., Andreu, D., Giralt, E., Navalpotro, C., Pedroso, E., Ponsati, B. and Ruiz-Gayo, M. (1989) Int. J. Peptide Res. 34, 124–128). The Npys-modified peptide is added to the peptide to be coupled having a terminal SH group and dissolved in 0.1 M sodium acetate, 0.1 M sodium chloride, pH 4.5, and the pH is then adjusted to 5.0 followed by incubation with stirring for at least 12 h. The pH is then adjusted to 7.0 by adding 1 N NaOH followed by another incubation for 3 h. After the reaction, the mixture is dialyzed against 10 mN $NaHCO_3$. The optimal pH range of the reaction is between 4.5 and 7.0. These conditions ensure minimization of unwanted side reactions such as, for example, formation of symmetric disulfides between the peptide molecules to be coupled or removal of the Npys group. The Npys-modified peptide should be present in the reaction in excess over the peptide to be conjugated (Albericio, F., Andreu, D., Giralt, E., Navalpotro, C., Pedroso, E., Ponsati, B. and Ruiz-Gayo, M. (1989) Int. J. Peptide Res. 34, 124–128).

Examples of the invention are illustrated in the following sequence listings:

SEQ ID NO.: 1 depicts an amino acid sequence derived from polyoma virus VP2, position 287–297. It serves in the synthetic biologically active molecule as anchor for anchoring the active substance to VP1.

SEQ ID NO.:2 depicts a first exemplary embodiment of a synthetic biologically active molecule. The HIV-1-derived peptide sequence corresponds to positions 1–21; the attached amino acid sequence acting as anchor occupies positions 22–33. It is derived from polyoma virus VP2.

SEQ ID NO.:3 depicts another example of an amino acid sequence suitable as anchor.

SEQ ID NO.:4 depicts the polyoma virus VP2 sequence. This shows the sequences between positions 250 and 300, which are suitable as anchors.

SEQ ID NOs.:5 and 6 show further synthetic biologically active molecules. They may be coupled with polyoma virus VP1 and then, for treatment of an HIV infection, be introduced into the infected cells.

What is claimed is:

1. A carrier, comprising:

a) a biologically active substance, wherein said biologically active substance is selected from the group consisting of a nucleic acid, an oligonucleotide, a protein, a peptide, a peptidic substance, a PNA, and a low molecular weight pharmaceutically-active substance, wherein said biologically active substance is coupled to b) an amino acid sequence (A1), wherein said A1 is from the C-terminal region of virus protein 2 (VP2) or 3 (VP3) of polyoma virus, wherein said A1 is not the full-length VP2 or VP3, wherein said A1 is associated with an amino acid sequence from virus protein 1 (VP1) of polyoma virus, thereby packaging said biologically active substance within a structured capsid carrier.

2. The carrier of claim 1, wherein said A1 is 10 to 55 amino acids in length.

3. The carrier of claim 1, wherein said A1 is 28 to 38 amino acids in length.

4. The carrier of claim 1, wherein said A1 comprises amino acid positions 250 to 319 of VP2 (SEQ ID NO:4).

5. The carrier of claim 1, wherein said A1 comprises amino acid positions 260 to 300 of VP2 (SEQ ID NO:4).

6. The carrier of claim 1, wherein said A1 comprises amino acid positions 287 to 297 of VP2 (SEQ ID NO:4).

7. The carrier of claim 1, wherein said A1 comprises the amino acid sequence:

```
Trp Met Leu Pro Leu Ile Leu Gly Leu Tyr Gly (SEQ ID NO:1)
 1              5                   10
```

8. The carrier of claim 1, wherein said biologically active substance is coupled to said A1 via a linker.

9. The carrier of claim 1, wherein said active substance and said A1 are encoded by one or more genetically engineered nucleic acid molecules.

10. A method for preparing a carrier, comprising the steps of:

a) providing an amino acid sequence (A1), wherein said A1 is from the C- terminal region of VP2 or VP3 of polyoma virus, wherein said A1 comprises a coupling agent;

b) binding a biologically active substance to said A1 via said coupling agent, wherein said biologically active substance is selected from the group consisting of a nucleic acid, an oligonucleotide, a protein, a peptide, a peptidic substance, a PNA, and a low molecular weight pharmaceutically-active substance; and c) contacting said A1 coupled to said biologically active substance with an amino acid sequence from VP1 of polyoma virus, thereby packaging said biologically active substance within a structured capsid carrier.

11. The method of claim 10, wherein said coupling agent comprises a glycine, a cysteine or a glycine-lysine.

12. The method of claim 10, wherein said coupling agent comprises an amino acid sequence (A2) bound to the N- or C-terminal end of said A1.

13. The method of claim 12, wherein said A2 comprises glycines and/or amino acids with functional side groups.

14. The method of claim 13, wherein said functional side groups are selected from the group consisting of amino, sulfhydryl, carboxyl, hydroxyl, guanidinium, phenyl, indole and imidazole radicals.

15. The method of claim 10, wherein said coupling agent is a reactive group, wherein said reactive group is bound to the C- or N-terminal end of said A1.

16. The method of claim 15, wherein said C- or N-terminal end of said A1 is an amino acid selected from the group consisting of glycine, cysteine and glycine-lysine.

17. The method of claim 15, wherein said reactive group comprises a monobromoacetyl radical, a monochloroacetyl radical, or a 3-nitro-2-pyridinesulfenyl radical (Npys).

18. The method of claim 10, wherein said biologically active substance is coupled to said A1 via a thioether or disulfide bridge.

19. The method of claim 12, wherein said biologically active substance is coupled to said A2 via a thioether or disulfide bridge.

20. The method of claim 10, wherein said biologically active substance is coupled to said A1 via a linker.

21. The method of claim 12, wherein said biologically active substance is coupled to said A2 via a linker.

22. The method of claim 10, wherein said A1 is 10 to 55 amino acids in length.

23. The method of claim 10, wherein said A1 is 28 to 38 amino acids in length.

24. The method of claim 10, wherein said A1 comprises amino acid positions 250 to 319 of VP2 (SEQ ID NO:4).

25. The method of claim 10, wherein said A1 comprises amino acid positions 260 to 300 of VP2 (SEQ ID NO:4).

26. The method of claim 10, wherein said A1 comprises amino acid positions 287 to 297 of VP2 (SEQ ID NO:4).

27. The method of claim 10, wherein said A1 comprises the amino acid sequence:

```
Trp Met Leu Pro Leu Ile Leu Gly Leu Tyr Gly (SEQ ID NO:1)
 1              5                   10
```

28. The method of claim 10, wherein said A1 and said biologically active substance are encoded by one or more genetically engineered nucleic acids.

29. The method of claim 10, wherein said biologically active substance is coupled to said A1 via a peptide.

30. A carrier, comprising:

a structured capsid formed from an amino acid sequence from virus protein 1 (VP1) of polyoma virus, wherein a biologically active substance is packaged within the structured capsid, wherein the biologically active substance is selected from the group consisting of a nucleic acid, an oligonucleotide, a protein, a peptide, a peptidic substance, a PNA, and a low molecular weight pharmaceutically-active substance, wherein the biologically active substance is coupled to an amino acid sequence (A1), wherein A1 is from the C-terminal region of virus protein 2 (VP2) or 3 (VP3) of polyoma virus, wherein said A1 is not full-length VP2 or VP3, wherein said A1 associates with said VP1, thereby forming said structured capsid.

31. The carrier of claim 30, wherein said A1 is 10 to 55 amino acids in length.

32. The carrier of claim 30, wherein said A1 is 28 to 38 amino acids in length.

33. The carrier of claim 30, wherein said A1 comprises amino acid positions 250 to 319 of VP2 (SEQ ID NO:4).

34. The carrier of claim 30, wherein said A1 comprises amino acid positions 260 to 300 of VP2 (SEQ ID NO:4).

35. The carrier of claim 30, wherein said A1 comprises amino acid positions 287 to 297 of VP2 (SEQ ID NO:4).

36. The carrier of claim 30, wherein said A1 comprises the amino acid sequence:

```
Trp Met Leu Pro Leu Ile Leu Gly Leu Tyr Gly (SEQ ID NO:1)
 1              5                   10
```

37. The carrier of claim 30, wherein said biologically active substance is coupled to said A1 via a linker.

38. The carrier of claim 30, wherein said active substance and said A1 are encoded by one or more genetically engineered nucleic acid molecules.

* * * * *

UNITED STATES PATENT AND TRADEMARK OFFICE

CERTIFICATE OF CORRECTION

PATENT NO. : 7,011,968 B1

APPLICATION NO. : 09/958451

DATED : March 14, 2006

INVENTOR(S) : Wolf Bertling, Christian Reiser and Jurgen Walter, PH.D.

It is certified that error appears in the above-identified patent and that said Letters Patent is hereby corrected as shown below:

Col 2 line 4
Title Page, References Cited, Other Publications, Shah reference, please delete "Oublishers" and insert --Publishers--therefor;

Col. 2 line 4
Title Page, References Cited, Other Publications, Shah reference, please delete "2996" and insert --1996--therefor;

Col. 2 line 7
Title Page, References Cited, Other Publications, Cole reference, please delete "Oublishers" and insert --Publishers--therefor;

Col. 2 line 7
Title Page, References Cited, Other Publications, Cole reference, please delete "2996" and insert --1996--therefor.

Signed and Sealed this

Fifth Day of September, 2006

JON W. DUDAS

*Director of the United States Patent and Trademark Office*

UNITED STATES PATENT AND TRADEMARK OFFICE

CERTIFICATE OF CORRECTION

PATENT NO. : 7,011,968 B1 
APPLICATION NO. : 09/958451
DATED : March 14, 2006
INVENTOR(S) : Wolf Bertling, Christian Reiser and Jurgen Walter It is certified that error appears in the above-identified patent and that said Letters Patent is hereby corrected as shown below:

Title Page, Assignee, please delete “november Aktiengesellchaft Gesellscaft fur Molekulare Medizin” and insert --responsif GmbH--therefor;

Signed and Sealed this

First Day of May, 2007

JON W. DUDAS
*Director of the United States Patent and Trademark Office*